United States Patent
Morrow et al.

(10) Patent No.: US 9,302,019 B2
(45) Date of Patent: Apr. 5, 2016

(54) FE(II) SEQUESTERING AGENTS AND USES THEREOF

(75) Inventors: Janet R. Morrow, Williamsville, NY (US); Pavel Tsitovich, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 0 days.

(21) Appl. No.: 14/116,275

(22) PCT Filed: May 11, 2012

(86) PCT No.: PCT/US2012/037608
§ 371 (c)(1),
(2), (4) Date: Nov. 7, 2013

(87) PCT Pub. No.: WO2012/155085
PCT Pub. Date: Nov. 15, 2012

(65) Prior Publication Data
US 2014/0072517 A1 Mar. 13, 2014

Related U.S. Application Data

(60) Provisional application No. 61/583,967, filed on Jan. 6, 2012, provisional application No. 61/583,039, filed on Jan. 4, 2012, provisional application No. 61/484,873, filed on May 11, 2011.

(51) Int. Cl.
| | | |
|---|---|---|
| *C07D 213/53* | (2006.01) | |
| *A61K 49/10* | (2006.01) | |
| *C07D 213/74* | (2006.01) | |
| *C07D 213/58* | (2006.01) | |
| *C07D 213/59* | (2006.01) | |
| *G01N 33/52* | (2006.01) | |
| *C07D 213/68* | (2006.01) | |
| *C07D 471/04* | (2006.01) | |

(52) U.S. Cl.
CPC ............ *A61K 49/106* (2013.01); *C07D 213/53* (2013.01); *C07D 213/58* (2013.01); *C07D 213/59* (2013.01); *C07D 213/68* (2013.01); *C07D 213/74* (2013.01); *C07D 471/04* (2013.01); *G01N 33/52* (2013.01)

(58) Field of Classification Search
CPC .............................. A61K 49/00; C07D 213/53
USPC ...................................................... 424/9.361
See application file for complete search history.

(56) References Cited

U.S. PATENT DOCUMENTS

| | | | |
|---|---|---|---|
| 4,657,903 A | 4/1987 | Scovill et al. | |
| 8,518,373 B2 * | 8/2013 | Aime et al. .................... | 424/9.3 |
| 2003/0129579 A1 | 7/2003 | Bornhop et al. | |
| 2005/0191243 A1 | 9/2005 | Aime et al. | |
| 2006/0057071 A1 | 3/2006 | Wong et al. | |
| 2008/0241074 A1 | 10/2008 | Bornhop et al. | |
| 2009/0142273 A1 | 6/2009 | Pagel et al. | |

OTHER PUBLICATIONS

Wolfgang Linert et al. Chromotropism Behavior and Biological Activity of some Schiff Base-Mixed Ligand Transition Metal complexes, Synthesis and Reactivity in Inorganic, Metal-Organic, and Nano-Metal Chemistry, 39, 570-599, 2009.*
Bernhard K. Keppler et al. Impact of Metal Coordination on Cytotoxicity of 3-Aminopyridine-2-carboxaldehyde Thiosemicarbazone (Triapine) and Novel Insights into Terminal Dimethylation, J. Med. Chem. 2009, 52, 5032-5043.*
Robert Muller et al. Spin Transition Molecular Materials: Intelligent Contrast Agents for Magnetic Resonance Imaging, JACS, 125, 8405-8407, 2003.*
Gerimario F. de Sousa et al., X-ray Crystallographic and Mossbauer Spectroscopic Applications in Dependence of Partial Quadrupole Splitting, [R], on the C—Sn—C-Angle in Seven-Coordinated Diorganotin(IV) Complexes, Inorg. Chem. 2006, 45, 4518-4525.*
Kasuga, N.C., et al., Synthesis, structural characterization and antimicrobial activities of 12 zinc(II) complexes with four thiosemicarbazone and two semicarbazone ligands, Journal of Inorganic Biochemistry, 2003, vol. 96, pp. 298-310.
De Sousa, G., et al., Crystallographic and Mossbauer Spectroscopic Applications in Dependence of Partial Quadrupole Splitting, [R], on the C—Sn—C Angle in Seven-Coordinated Diorganotin(IV) Complexes, Inorganic Chemistry, Apr. 25, 2006, vol. 45, pp. 4518-4525.
Kowol, C., et al., Impact of Metal Coordination on Cytotoxicity of 3-Aminopyridine-2-carboxaldehyde Thiosemicarbazone (Triapine) and Novel Insights into Terminal Dimethylation, Journal of Medicinal Chemistry, Jul. 28, 2009, vol. 52, No. 16, pp. 5032-5043.
Kowol, C., et al., Effect of metal ion complexation and chalcagon donor identiy on the antiproliferative activity of 2-acetylpyridine N,N-dimethyl(chalcogen)semicarbazones, Journal of Inorganic Biochemistry, Jul. 31, 2007, vol. 101, pp. 1946-1957.
Muller et al. J. Am. Chem. Soc. 2003, 125, 8405-8407.
Mandal et al. Inorg,. Chem. 1997, 36 5424-5425. 1.
Zhang et al. J. Am. Chem. Soc. 2005, 127, 17572-17573.
Himmelreich et al. Methods 2009, 48, 112-124.

* cited by examiner

*Primary Examiner* — Michael G Hartley
*Assistant Examiner* — Jagadishwar Samala
(74) *Attorney, Agent, or Firm* — Hodgson Russ LLP

(57) ABSTRACT

Compounds and uses of the compounds are provided. The compounds can be used as Fe(II) sequestering compounds. For example, these compounds can be used to sequester Fe(II) in cells, organs, vasculature, or tissues. Also, provided are compositions and methods of using the them for sequestering Fe(II) in an individual. The compounds can be used as MRI paraCEST contrast agents.

16 Claims, 8 Drawing Sheets compd 1　　　　　　　compd 2　　　　　　　compd 3

FE(II) SEQUESTERING AGENTS AND USES THEREOF

CROSS-REFERENCE TO RELATED APPLICATIONS

This application claims priority to U.S. provisional patent application No. 61/484,873, filed May 11, 2011, U.S. provisional patent application No. 61/583,039, filed Jan. 4, 2012, and U.S. provisional patent application No. 61/583,967, filed Jan. 6, 2012, the disclosures of which are incorporated herein by reference.

FIELD OF THE INVENTION

The present invention generally relates to methods of sequestering Fe(II). More particularly, it relates to sequestering Fe(II) in an individual using the compounds of the present invention.

BACKGROUND OF THE INVENTION

Iron has a crucial role in biology; thus, alterations from homeostatic levels of iron, either high or low, are detrimental to health. Commonly occurring diseases that involve aberrant iron homeostasis include chronic hemochromatosis and thalassaemia in which excess iron accumulation leads to iron deposits in heart and liver. Abnormally high iron levels in the brain correlate with a number of neurological disorders including Alzheimer's, Huntington's chorea, Friedreich's ataxia, Parkinson's disease and multiple sclerosis. For example, a hallmark of patients with Parkinson's disease is increased iron content in glial cells and dopaminergic neurons. In these diseases, excess iron may have a role in the progressive deterioration observed in patients. In addition, brain micro-bleeds lead to the deposit of excess iron. Such microbleeds have been attributed as one of the causes of dementia including Alzheimer's. It has been estimated that more than 5% of the population over 65 has either Parkinson's or Alzheimer's disease.

Clinical trials are underway to give patients chelating ligands to treat neurological disorders. There is a critical need for in vivo sensors that would track the effect of chelating drugs on brain iron levels. Iron levels in different areas of the brain may be diagnostic of neurological disorders.

MRI is the method of choice for monitoring high levels of iron in organs. Excess iron deposits are detected in organs such as heart, liver and brain by using MRI techniques that capitalize on differences in bulk water proton relaxivity in tissues that contain excess iron. This includes magnetic susceptibility imaging, and T2 and T1 weighted MR images. These methods, however, suffer from artifacts such as areas of calcification that can complicate interpretation. More direct imaging methods are needed that would register both the iron oxidation state and distribution in tissue. New methods for the detection and imaging of specific iron species may open up new avenues of research on human diseases that involve iron mismanagement.

BRIEF SUMMARY OF THE INVENTION

In an embodiment, the present invention provides a compound having the following structure:

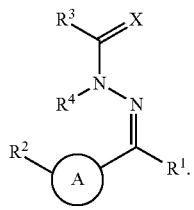

is a $C_2$ to $C_{12}$ heterocyclic ring system with at least one heteroatom selected from the group consisting of: N atom, O atom, and S atom. $R^1$ is selected from the group consisting of: H and $C_1$ to $C_{12}$ alkyl group. $R^2$ is selected from the group consisting of: H, $NH_2$, $CH_2C(O)NH_2$, and $CH_2(OCH_2CH_2)_nOCH_2CH_3$, where n is from 1 to 6 or $R^2$ is

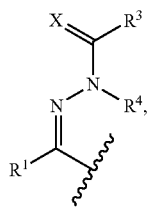

where $R^3$ is selected from the group consisting of: $NH_2$, $N(R^5)_2$, and

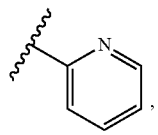

and $R^4$ is H or $C_1$ to $C_{12}$ alkyl group. Each $R^5$ is independently selected from H and $C_1$ to $C_{12}$ alkyl group, and X is O or S. The compound has at least one exchangeable proton. Optionally, the compound has an Fe(II) cation complexed to the compound.

In an embodiment, the compound has the following structure:

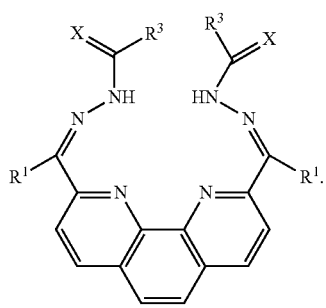

$R^1$ is H or a $C_1$ to $C_{12}$ alkyl group, $R^3$ is $NH_2$ or $N(CH_3)_2$, and X is O or S.

In an embodiment, the compound has the following structure:

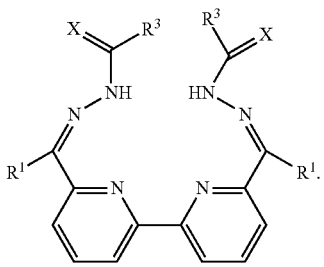

$R^1$ is H or a $C_1$ to $C_{12}$ alkyl group, $R^3$ is $NH_2$ or $N(CH_3)_2$, and X is O or S.

In an embodiment, the present invention provides a method to obtain an image of at least a portion of a cell, organ, vasculature, or tissue comprising the steps of: contacting the cell, organ, vasculature, or tissue with a compound of the present invention, and imaging at least a portion of the cell, organ, vasculature, or tissue to obtain a magnetic resonance image of the portion of the cell, organ, vasculature or tissue, where the image is obtained by magnetic resonance imaging. The cell, organ, vasculature, or tissue can be part of an individual. The at least a portion of the compound can complex with endogenous Fe(II) and an image showing the endogenous Fe(II) sequestered by the compound can be obtained.

DETAILED DESCRIPTION OF THE INVENTION

Figure 1:
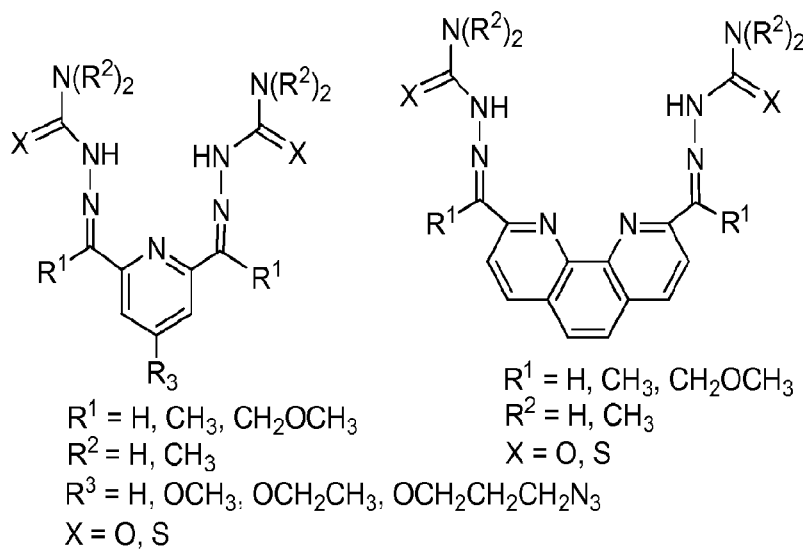
FIG. 1. Representative CEST spectrum of the 3 mM Fe(II) complex shown at pH 7.6 and 6.0.
Figure 2:
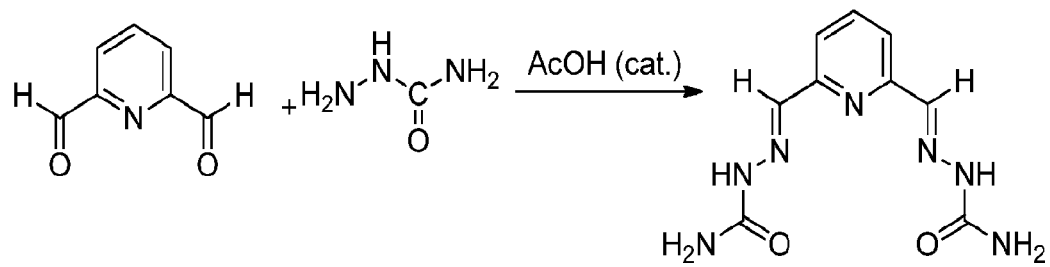
FIG. 2. An example of a synthesis of a pentadentate semicarbazide ligand.

The present invention provides compounds that can sequester Fe(II). To overcome the limitations and critical needs for sensing and tracking iron levels in cells, organs, vasculatures and tissues, compounds that can be used to image iron in tissue in vivo are disclosed. Methods of imaging using those agents are also disclosed. For example, the compounds can be used in imaging applications such as MRI paraCEST as contrast agents, or as, agents for MRSI. Applications of these agents include temperature sensing (thermometry), and pH mapping. Monitoring excess iron levels in at least part of a cell, organ, vasculature, or tissue will facilitate tracking and treatment of a number of diseases where iron plays a critical role.

The present invention is based on the surprising result that the compounds selectively sequester Fe(II) over Fe(III).

As used herein unless expressly defined otherwise, "alkyl group" refers to branched or unbranched saturated hydrocarbons. Examples of such alkyl groups include methyl groups, ethyl groups, butyl groups, nonyl groups, neopentyl groups, and the like. For example, the alkyl group can be a $C_1$ to $C_{12}$ alkyl group, including all integer numbers of carbons and ranges of numbers of carbons therebetween. The alkyl group can be unsubstituted or substituted with, for example, an oxygen atom (e.g., forming an ether linkage), a nitrogen atom (e.g., an amine), azides, alkyl phosphonium salts, or a combination thereof. The substitution on the alkyl group can be chiral, achiral, or a combination thereof.

As used herein, "heterocyclic ring system" refers to a cyclic compound having a ring or multiple rings in which at least one of the atoms forming the ring(s) is a heteroatom (e.g., oxygen, nitrogen, sulfur, etc.). The ring(s) of the heterocyclic ring system can be aromatic or nonaromatic, and include compounds that are saturated, partially unsaturated, or fully unsaturated. The ring(s) of the heterocyclic ring system can be fused or separated by a single bond (e.g., biaryl, bipyridyl, etc.). Examples of the heterocyclic ring systems include pyridyl, 2,2'-bipyridyl, phenanthrolyl, piperidinyl, pyrimidine, triazine, pyrazine, benzoimidazole, pyridazine, triazine, imidazole, thiadiazole, thiazole, oxazole, oxadiazole, triazole, quinolone, isoquinoline, thiophenyl, furanyl, tetrahydrofuranyl, and the like. For example, the heterocyclic ring system can have from $C_2$ to $C_{12}$ number of carbons, including all integer numbers of carbons and ranges of numbers of carbons there between. The heterocyclic ring systems can be substituted with, for example, $C_1$ to $C_{12}$ alkyl group (e.g., Me, Et, Pr, i-Pr, t-Butyl), PEG group (—(OCH$_2$CH$_2$)$_n$OH), —(OCH$_2$CH$_2$)$_n$OCH$_3$), —(OCH$_2$CH$_2$)$_n$OCH$_2$CH$_3$)), or thioether group (—(SCH$_2$CH$_2$)$_n$SH), —(SCH$_2$CH$_2$)$_n$SCH$_3$), —(SCH$_2$CH$_2$)$_n$SCH$_2$CH$_3$), where n is from 1 to 6, halogen atom (e.g., F, Cl, Br, I), —C≡CH, Phenyl, —CF$_3$, —CN, —CH$_2$Cl, —CH$_2$F, —CHF$_2$, —OH, —OMe, —OEt, —OPr, —OiPr, —OCF$_3$, —CH$_2$OH, —CH$_2$OMe, —CH(OH)Me, —CH(OH)Et, —C(OH)Me$_2$, —CH$_2$NH$_2$, —CH$_2$NHMe, —CH(NH$_2$)Me, —CH(NH$_2$)Et, —C(NH$_2$)Me$_2$, —B(OH)$_2$, —NH$_2$, —NHMe, —NHEt, —NHPr, —NMe$_2$, —SMe, —SEt, —NO$_2$, —NHSO$_2$Me, —(CO)NH$_2$, —(CO)NHMe, —(CO)NMe$_2$, —COOMe, —COOEt, —COOOH, —COMe, substituted or unsubstituted C$_1$ to C$_{12}$ aryl, and substituted or unsubstituted C$_1$ to C$_{12}$ heterocycle, where substitution is possible on the ring system by adhering to the common valences for the main group elements.

In an embodiment, the present invention provides a compound having at least one heteroatom in a heterocyclic ring system. In an embodiment, the present invention provides Fe(II) sequestering compounds having the following structure:

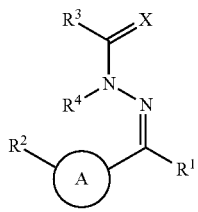

where R$^1$ is selected from the group consisting of: H and C$_1$ to C$_{12}$ alkyl group, R$^2$ is selected from the group consisting of: H, NH$_2$, CH$_2$C(O)NH$_2$, and CH$_2$(OCH$_2$CH$_2$)$_n$OCH$_2$CH$_3$, where n is from 1 to 6, or
R$^2$ is

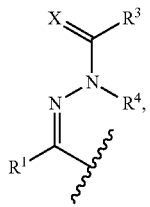

where R$^3$ is selected from the group consisting of: NH$_2$, N(R$^5$)$_2$, and

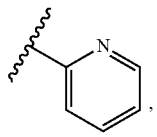 [SMILES: *c1ccccn1]

R$^4$ is H or C$_1$ to C$_{12}$ alkyl group, each R$^5$ is independently selected from H and C$_1$ to C$_{12}$ alkyl group, and X is O or S. In an embodiment, the substituents on the heterocyclic ring system also apply to R$^1$ and R$^2$.

is a C$_2$ to C$_{12}$ heterocyclic ring system with at least one heteroatom selected from the group consisting of: N atom, O atom, and S atom. The heterocyclic ring system can be further substituted with, for example, C$_1$ to C$_{12}$ alkyl group (e.g., Me, Et, Pr, i-Pr, t-Butyl), PEG group (—(OCH$_2$CH$_2$)$_n$OH), —(OCH$_2$CH$_2$)$_n$OCH$_3$), —(OCH$_2$CH$_2$)$_n$OCH$_2$CH$_3$)), or thioether group (—(SCH$_2$CH$_2$)$_n$SH), —(SCH$_2$CH$_2$)$_n$SCH$_3$), —(SCH$_2$CH$_2$)$_n$SCH$_2$CH$_3$), where n is from 1 to 6, halogen atom (e.g., F, Cl, Br, I), —C≡CH, Phenyl, —CF$_3$, —CN, —CH$_2$Cl, —CH$_2$F, —CHF$_2$, —OH, —OMe, —OEt, —OPr, —OiPr, —OCF$_3$, —CH$_2$OH, —CH$_2$OMe, —CH(OH)Me, —CH(OH)Et, —C(OH)Me$_2$, —CH$_2$NH$_2$, —CH$_2$NHMe, —CH(NH$_2$)Me, —CH(NH$_2$)Et, —C(NH$_2$)Me$_2$, —B(OH)$_2$, —NH$_2$, —NHMe, —NHEt, —NHPr, —NMe$_2$, —SMe, —SEt, —NO$_2$, —NHSO$_2$Me, —(CO)NH$_2$, —(CO)NHMe, —(CO)NMe$_2$, —COOMe, —COOEt, —COOOH, —COMe, substituted or unsubstituted C$_1$ to C$_{12}$ aryl, and substituted or unsubstituted C$_1$ to C$_{12}$ heterocycle. In an example, the heterocyclic ring system can have 1, 2, 3, 4, 5 nitrogen atoms. In an example, the heterocyclic ring system can have 1, 2, 3, 4, or 5 oxygen atoms. In an example, the heterocyclic ring system can have 1, 2, 3, 4, or 5 sulfur atoms. In an example, the heterocyclic ring system can have a combination of 1, 2, 3, 4, or 5 oxygen atoms, nitrogen atoms, and sulfur atoms.

In an embodiment,

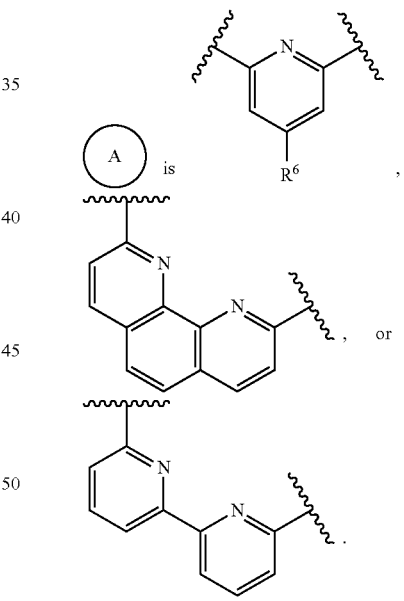

R$^6$ is selected from the group consisting of: H, C$_1$ to C$_{12}$ alkyl group, ether group, or amino group. In an example, the heterocyclic ring system can be further substituted with, for example, C$_1$ to C$_{12}$ alkyl group (e.g., Me, Et, Pr, i-Pr, t-Butyl), PEG group containing oxygen (—(OCH$_2$CH$_2$)$_n$OH), —(OCH$_2$CH$_2$)$_n$OCH$_3$), —(OCH$_2$CH$_2$)$_n$OCH$_2$CH$_3$)), or thioether (—(SCH$_2$CH$_2$)$_n$SH), thioether —(SCH$_2$CH$_2$)$_n$SCH$_3$), —(SCH$_2$CH$_2$)$_n$SCH$_2$CH$_3$), where n is from 1 to 6, halogen atom (e.g., F, Cl, Br, I), —C≡CH, Phenyl, —CF$_3$, —CN, —CH$_2$Cl, —CH$_2$F, —CHF$_2$, —OH, —OMe, —OEt, —OPr, —OiPr, —OCF$_3$, —CH$_2$OH, —CH$_2$OMe, —CH(OH)Me, —CH(OH)Et, —C(OH)Me$_2$, —CH$_2$NH$_2$, —CH$_2$NHMe, —CH(NH$_2$)Me, —CH(NH$_2$)Et, —C(NH$_2$)

Me₂, —B(OH)₂, —NH₂, —NHMe, —NHEt, —NHPr, —NMe₂, —SMe, —SEt, —NO₂, —NHSO₂Me, —(CO)NH₂, —(CO)NHMe, —(CO)NMe₂, —COOMe, —COOEt, —COOOH, —COMe, substituted or unsubstituted C₁ to C₁₂ aryl, and substituted or unsubstituted C₁ to C₁₂ heterocycle in place of a H atom on the ring(s). The substitution can include groups that are chiral, achiral, or combinations thereof.

In an embodiment, the compound has the following structure:

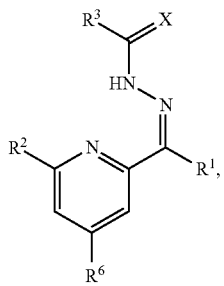

where R¹ is H, a C₁ to C₁₂ alkyl group, R² is H, R³ is NH₂, and R⁶ is H, an amino group, C₁ to C₁₂ alkyl group, or ether group, and X is O or S.

In an embodiment, the compound has the following structure:

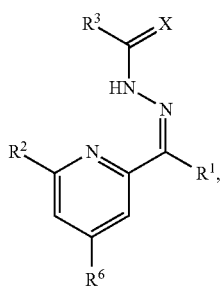

where R¹ is H, a C₁ to C₁₂ alkyl group, R² is NH₂ or CH₂C(O)NH₂, R³ is

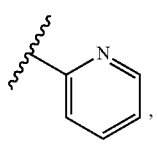 [SMILES: *c1ccccn1]

R⁶ is H, an amino group, C₁ to C₁₂ alkyl group, or ether group, and X is O or S.

In an embodiment, the compound has the following structure:

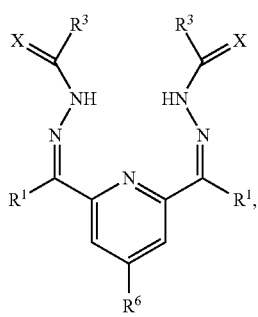

where R¹ is H, a C₁ to C₁₂ alkyl group, R³ is NH₂ or N(CH₃)₂, R⁶ is H, an amino group, C₁ to C₁₂ alkyl group, or ether group, and X is O or S.

In an embodiment, the compound has the following structure:

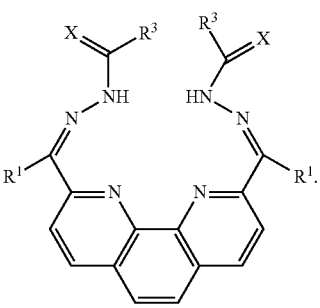

where R¹ is H, a C₁ to C₁₂ alkyl group, R³ is NH₂ or N(CH₃)₂, and X is O or S.

In an embodiment, the compound has the following structure:

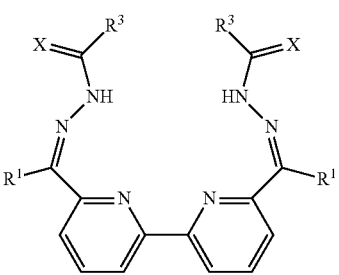

where R¹ is H, a C₁ to C₁₂ alkyl group, R³ is NH₂ or N(CH₃)₂, and X is O or S.

In an embodiment, the compound has the following structure:

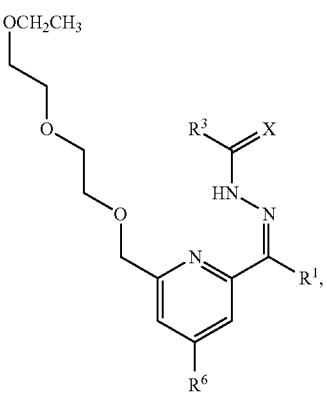

where R¹ is H, a C₁ to C₁₂ alkyl group, R³ is NH₂ or N(CH₃)₂, and X is O or S.

Examples of suitable compounds include:

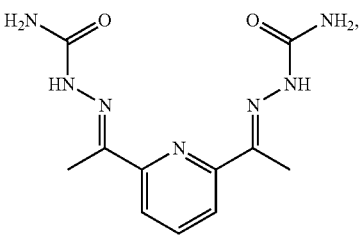

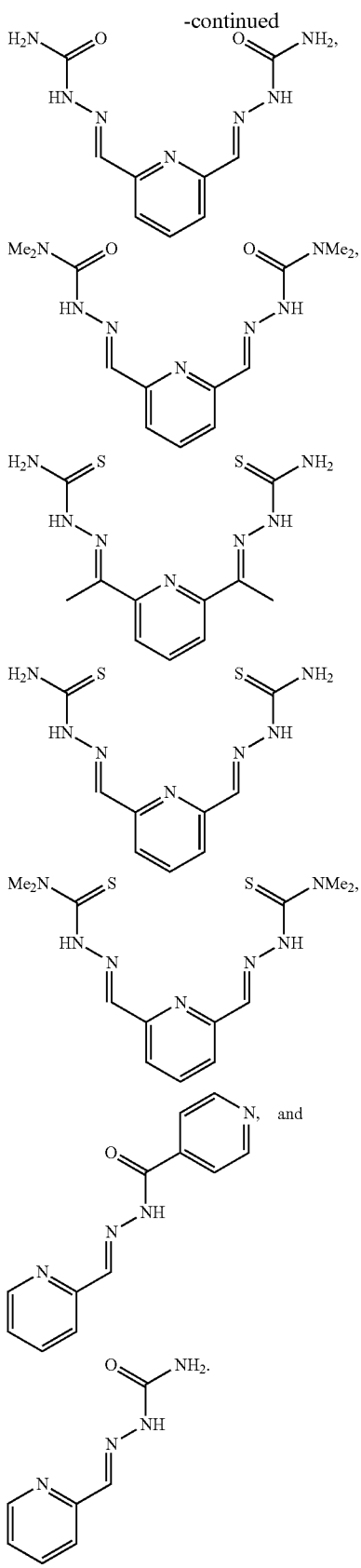

In an embodiment, the compounds of the invention can be complexed to a Fe(II) cation.

In various embodiments, the compounds of the invention are a salt, a partial salt, a hydrate, a polymorph, a stereoisomer or a mixture thereof. The compounds can have stereoisomers. For example, the compound can be present as a racemic mixture, a single enantiomer, a single diastereomer, mixture of enantiomers, or mixture of diastereomers.

The compounds of the invention can be used to sequester the Fe(II) from cells for imaging. In an embodiment, the compounds bind selectively to Fe(II) over Fe(III). The compounds described herein sequester endogenous iron in cells and possess the ability to image certain forms of iron even in the presence of other metal ions and cellular components. In an embodiment, the compounds of the present invention are those that bind Fe(II) under physiologically relevant conditions and can be used in an imaging method using for paramagnetic chemical exchange transfer (paraCEST). The compounds and methods of the present disclosure will give information about chelatable Fe(II) in the brain and other organs. For example, iron overload diseases accumulate iron in the liver and/or heart and the amount of iron correlates with the health of patient. In an embodiment, the application of the compounds include the detection of tumors, heat ablation of tumors and diagnosis of metabolic abnormalities.

Figure 8:
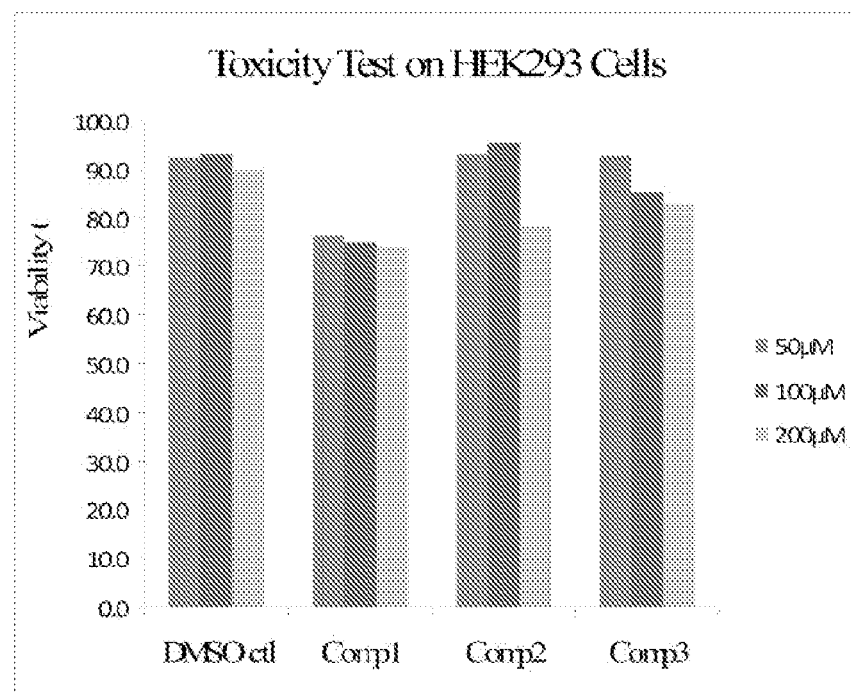
FIG. 8. An example of a toxicity test on kidney cells (HEK293) showing cell viability for cells incubated in the presence of 50, 100 and 200 micromolar compound.
Figure 8:
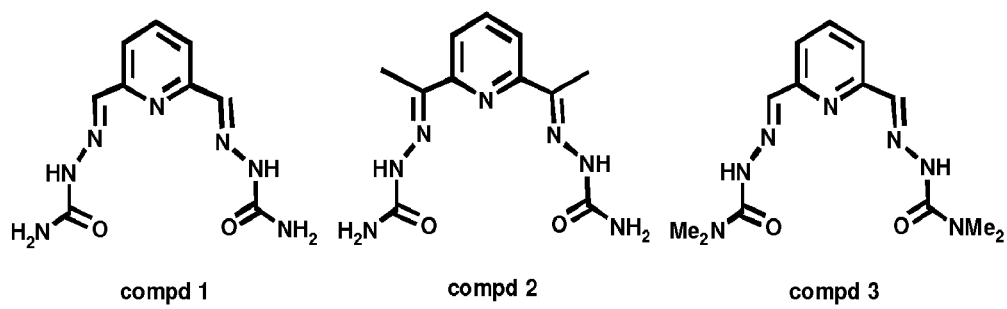

Administering the compound allows for the sequestering of Fe(II). The compounds of the present invention, therefore, do not sequester transferrin bound iron as this iron exists as Fe(III). The compounds sequester Fe(II) such that a stable complex is formed and dissociation of the Fe(II) can be prevented. When the compound is administered to an individual, the toxicity is extremely low (i.e., to the kidney) and safety to the individual is high. An example of the low toxicity of the compounds are shown in FIG. 8.

ParaCEST agents give negative MRI contrast which can be turned on and off through frequency selective irradiation of an exchangeable proton resonance on the contrast agent. The paraCEST effect was observed in the presence of Fe(II) and the signal will vary according to the oxidation state of iron and geometry of the iron-complex. The compounds of the invention can have exchangeable protons. In an embodiment the compounds have from 1 to 8 exchangeable protons. The optimal rate constant is ($k_{CE}$) is as large as possible as long as the $^1$H NMR spectrum is in slow to intermediate exchange (i.e., the rate constant (units s$^{-1}$ or Hz) may not be larger than the separation between the bulk water protons and the exchangeable protons ($\Delta\omega$ in Hz) as in Eq. 1.

$$\Delta\omega \geq k_{CE} \qquad \text{Eq. 1}$$

In an embodiment, the sequestered Fe(II) is high spin (i.e., paramagnetic). For PARACEST, a paramagnetic spin state is needed. In order to keep Fe(II) in the high spin state, the ligand (or crystal) field splitting must not be too large. If the crystal field splitting is larger than the pairing energy, a diamagnetic low spin state will result.

The paramagnetic induced proton shifts of the Fe(II) complexes are dependent on a number of factors. Paramagnetic induced proton shifts (PIPS) arise from contact (through-bond) and pseudocontact (through-space, dipolar) contributions. These contributions are in addition to inductive diamagnetic effects which are inherent within the compounds of the present invention but are relatively small (Eq. 2):

$$\delta_{PIPS} = \delta_{cont} + \delta_{pseudo} + \delta_{dia} \qquad \text{Eq. 2}$$

Transition metal ions with moderately large anisotropic magnetic moments have strong dipolar contributions to PIPS. However, potentially larger contact shifts are anticipated with transition metal ions due to the larger degree of covalency in their metal-ligand bonds. Dipolar shift contributions are a result of through space interactions between the unpaired electrons and the nucleus. They are dependent on the distance of the proton from the metal ion center, the magnitude of the magnetic anisotropy tensor and the angle of the proton with respect to the principal axis of the magnetic susceptibility tensor. Large dipolar shifts are generally observed for protons that are 2-3 bonds away from the metal ion center. Contact shifts are proportional to the unpaired spin density at the proton. Spin density arises from a combination of direct delocalization and spin polarization. Contact shifts are dependent on the hyperfine coupling constant and the spin expectation value as transmitted through bonds. Contact shifts may have an impact on PIPS over relatively long distances, especially in conjugated systems. In an embodiment, primarily contact shifts occur over 3 to 5 bonds from the Fe(II) center. In an example, the dipolar and contact shift contributions of paramagnetic Fe(II) complexes make it feasible to use donor groups with (proximal) exchangeable protons such as the NH of amides as well as more remotely located groups connected through a ligand pi system such as amino-pyridines.

The necessary solubility of the complexes depends on their effectiveness in producing contrast. For paraCEST contrast agents that have CEST peaks shifted greater than 120 ppm from the proton resonance of bulk water, the complexes need 20 to 100 µM (micromolar) solubility. For paraCEST complexes that have peaks of less than 100 ppm, solubility must be in the low milimolar range. For Fe(II) complexes used for magnetic resonance spectroscopy imaging (MRSI), complexes should have solubilities of 1-20 mM. Solubility is generally measured in aqueous solution at near neutral pH (6.5 to 7.5) in 100 mM NaCl with 25 mM carbonate and 0.4 mM phosphate.

In an aspect, the present invention provides imaging methods using the macrocyclic compounds. In an embodiment, the invention provides a method to obtain an image of at least a portion of a cell, organ, vasculature, or tissue comprising the steps of: contacting a cell, organ, or tissue with the compounds of the invention, and imaging at least a portion of the cell, organ, vasculature, or tissue to obtain an image of the portion of cell, organ, vasculature, or tissue.

In an embodiment, the portion of a cell, organ, or tissue is part of an individual. By "individual" it is meant a human or non-human mammal. The at least part of a cell, tissue, or organ can be alive or dead. Likewise, the individual can also be alive or deceased.

In an embodiment, the image of the method can be obtained by a variety of imaging techniques. The techniques use magnetic resonance imaging. In an embodiment, the imaging technique can be Magnetic Resonance Imaging (MRI). In an embodiment, the disclosed compounds will act as MRI contrast agents through paramagnetic chemical exchange saturation transfer (paraCEST), and the disclosed methods can utilize the same.

In an embodiment, the imaging technique can use MRSI (also referred to herein as CSI). MRSI is used to measure the levels of different metabolites in body tissues. The MR signal produces a spectrum of resonances that correspond to different molecular arrangements of the isotope being "excited". In an embodiment, the compounds can be used in Magnetic resonance spectroscopic imaging (MRSI). In an embodiment, the imaging technique can be MRSI. MRSI combines both spectroscopic and imaging methods to produce spatially localized spectra for each voxel from within the sample or patient. The spatial resolution is much lower (limited by the available signal to noise ratio and memory availability for data storage), but the spectra in each voxel contains information about many metabolites. The proton NMR spectrum of the complexes in solutions containing 100 mM NaCl, 25 mM carbonate, 0.4 mM phosphate as a function of temperature (FIGS. 3 and 4) on a high field NMR spectrometer (300-500 MHz) were obtained. The spectra were acquired and averaged for about 10 minutes and a proton NMR spectrum was obtained. The spectrum will be created by using multi-voxel spectroscopic techniques and water suppression.

In an embodiment, the Fe(II) complex of the method can be a Chemical Exchange Saturation Transfer (CEST) agent. CEST exploits the ability of Nuclear magnetic Resonance (NMR) to resolve different signals arising from protons on different molecules. By selectively saturating a particular proton resonance of the compounds of the present disclosure that is in exchange with the surrounding water molecules, the MRI signal from the surrounding bulk water is also attenuated. A requirement for off-resonance saturation is that chemical exchange of the proton between contrast agent and water must be in the intermediate regime where exchange is fast enough to efficiently saturate the bulk water signal but slow enough on the NMR timescale to retain two proton resonances. In other words, there is a chemical shift difference between the exchangeable proton and the bulk water proton resonances. Paramagnetic metal ions (such as iron) shift the proton ($^1$H) resonances of substituents that bind to them. Design of a paraCEST agent involves incorporation of at least one exchangeable proton into the compound. The exchangeable proton should be placed such that its $^1$H resonance is shifted substantially by interaction with the iron. Application of a frequency selective presaturation pulse at the resonance of the exchangeable proton prior to the NMR spectroscopy experiment gives rise to the paraCEST spectrum which maps the water proton intensity as a function of presaturation pulse frequency. In an embodiment, the difference between the bulk water signal and the exchangeable proton is from 40 to 250 ppm, from the proton resonance of bulk water. It is important to produce exchangeable proton resonances that are sufficiently shifted from bulk water to avoid the endogenous macromolecule magnetization transfer (MT) effect. Obtaining the highly shifted proton resonance (large Acs from bulk water) that would avoid sensitivity loss in vivo due to endogenous MT has been a difficult hurdle to overcome. Shifting the exchangeable proton resonance by >120 ppm away from the bulk water resonance will lead to more sensitive contrast agents that will enable their development for pH and temperature sensing by avoiding MT effects.

The detection sensitivity of CEST agents depends on several factors including the rate constant for proton exchange, the number of exchangeable protons, the concentration of the contrast agent, the value of $T_1$ for water protons in the presence of the agent and the pulse power and duration. Eq. 3 is derived from the assumption that the magnetization of the exchangeable proton is saturated and defines the CEST effect as the net reduction in the water magnetization ($M_z/M_o$).

$$\frac{M_Z}{M_0} = \frac{1}{1 + k_1 T_1} \qquad \text{Eq. 3}$$

$$k_1 = n[\text{agent}]k_{CE}$$

where $k_{CE}$ is the single site exchange rate, n is the number of exchangeable protons/molecule, and $T_1$ is the water spin-lattice relaxation time in the presence of the saturating pulse. A large n is accomplished by incorporating symmetry into the macrocyclic compound.

In an embodiment, the macrocyclic compound of the method can be a paraCEST agent. ParaCEST is a novel contrast mechanism that is important during in vivo imaging due to the complex biological environment. Studies of these compounds have revealed that, in solution, MRI was able to reliably image agents designed to detect iron(II).

In another embodiment, the iron(II) compound of the method can be a thermometry agent. The compounds disclosed are ideal for development as a temperature dependent MRS agent for an application known as thermometry—temperature sensing in vivo. The change in the chemical shift of the proton resonances of paramagnetic metal ion complexes is proportional to temperature over a narrow temperature range. In another embodiment, the compounds disclosed will be used for temperature dependent chemical shift imaging (thermometry). The proton resonances must be relatively sharp for the experiment to have a good signal to noise ratio; broad peaks are hard to image with high signal to noise. It is beneficial to irradiate the proton resonances with greatest number of equivalent protons (i.e., $CH_3$) and have them be highly shifted for imaging in thermometry. It is preferred that thermometry agents have large temperature coefficients (CT, chemical shift change per degree=$\Delta\delta/°$ C.) and narrow linewidths (FWHM) to distinguish small temperature changes of 0.05° C. to 0.5° C. A useful parameter is CT/FWHM which takes into account both shift with temperature and linewidth. In an embodiment, the CT/FWHM of the compounds of the invention is 0.3 to 5.0. In addition, the protons used for thermometry should be shifted at least 30 ppm from bulk water.

In this application, the highly shifted proton resonances of the Fe(II) complexes are monitoring for magnetic resonance imaging. Some of the Fe(II) complexes are suitable as dual paraCEST MR imaging contrast agents and chemical shift imaging agents.

In yet another embodiment, the Fe(II) compound of the method can be a pH mapping agent. The compounds of the invention can be used as pH probes in at least a portion of a cell. In an embodiment, at least a portion of the cell can be part of a brain. In an embodiment, the at least portion of a cell can be a tumor cell. In addition to being temperature dependent, the non-exchangeable proton resonances of paramagnetic complexes may be pH dependent. Compounds that have proton resonances that vary with both pH and temperature have been developed for simultaneous pH and temperature sensing. In another embodiment, the compounds are dual paraCEST/thermometry agents.

Figure 9:
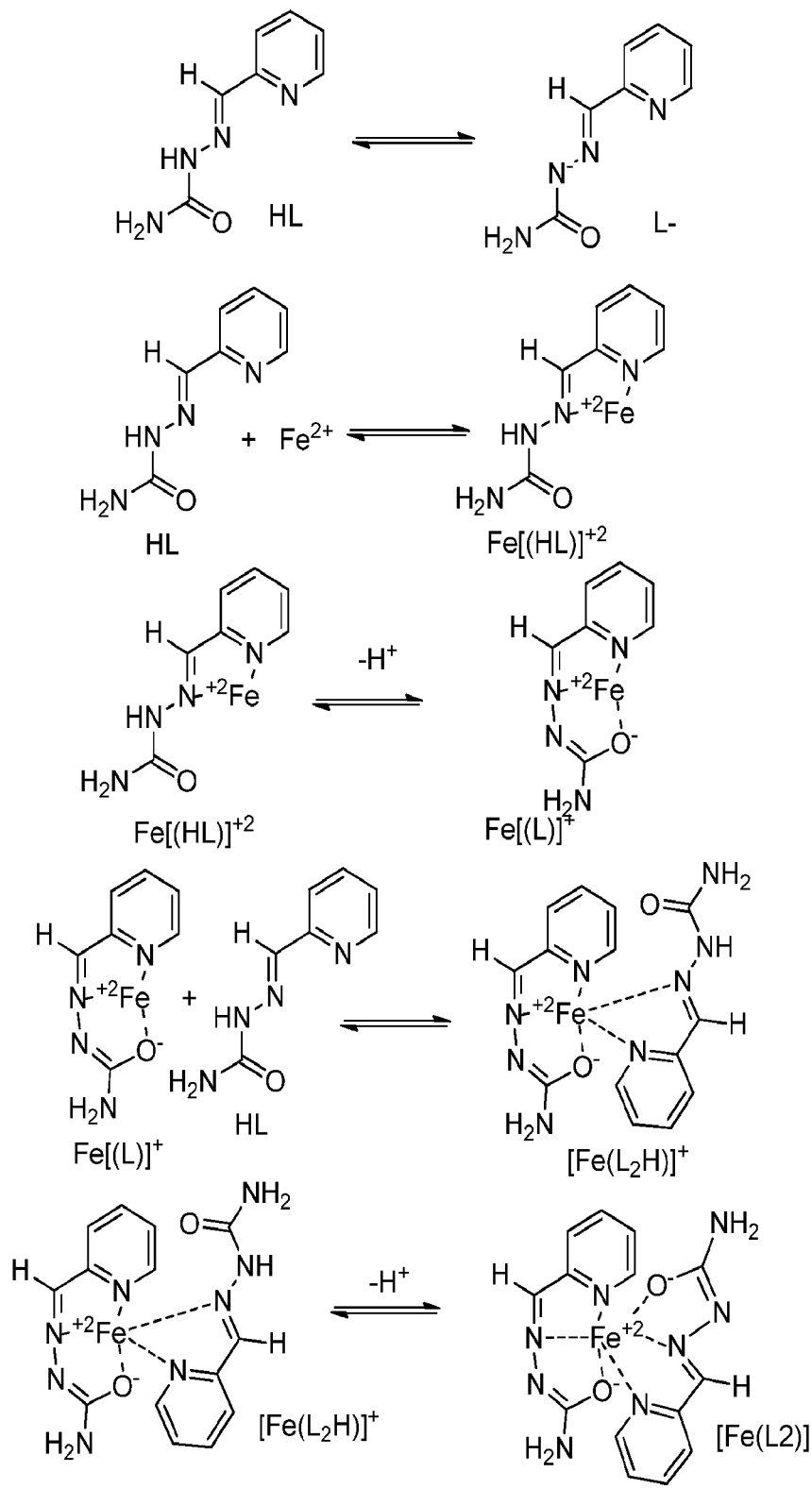
FIG. 9. The Fe(II) complexes formed upon binding of tridentate semicarbazide ligand.

The dissociation constant for the Fe(II) complexes of the compounds of the invention are in the milimolar to micromolar range in water at neutral pH. For example, see binding isotherm for DAPSC with Fe(II) shown in FIG. 6. Conditions are pH 7.6 and 100 mM NaCl. Tridentate ligands have binding constants that are typically 100-fold weaker. The binding constants depend strongly on pH. At pH values between 6 and 8, the ligands are protonated and are neutral. Most important, there are different Fe(II) complexes that form as a function of pH (FIGS. 8 and 9). The metal ions bind to initially give cationic complexes at weakly acidic pH (6) ([Fe(HL)]$^{2+}$ and [Fe(H$_2$L)]$^{2+}$. At neutral to slightly basic pH, the prominent form is the neutral Fe(II) complex with deprotonated ligand (Fe(L)$_2$ or Fe(L1) FIGS. 8, 9). Note that one or two tridentate ligands may bind to Fe(II).

Figure 5:
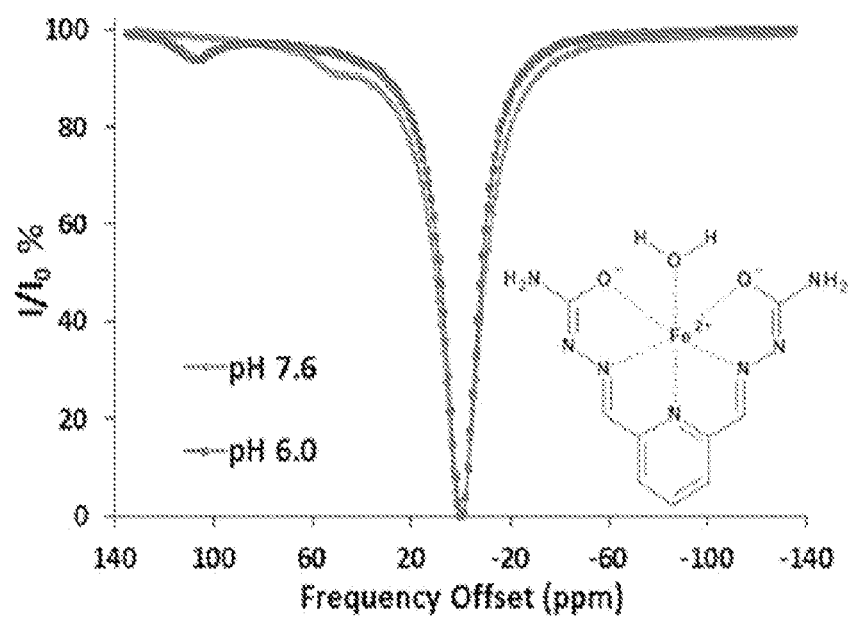
FIG. 5. Representative CEST spectrum of Fe(II) semicarbazide complex at pH 6.0 and 7.6. The two CEST peaks show that this complex may be useful as a pH switch.

There are different Fe(II) complexes of different protonation states at different pH values. These different protonation states give Fe(II) complexes with distinct NH exchangeable protons. For this reason, the complexes have pH dependent CEST spectra (FIG. 5). These complexes are useful for development as pH switches.

For use in the invention, the compositions described herein can be administered as pharmaceutical preparations. Thus, they can be provided in a variety of solutions of various compositions, and can be combined with one or more standard pharmaceutically acceptable carriers. Some examples of pharmaceutically acceptable carriers can be found in: *Remington: The Science and Practice of Pharmacy* (2005) 21st Edition, Philadelphia, Pa. Lippincott Williams & Wilkins.

Various methods known to those skilled in the art may be used to introduce the compositions of the invention to an individual. These methods include but are not limited to intravenous, intramuscular, intracranial, intrathecal, intradermal, subcutaneous, and oral routes. In one embodiment, the composition is administered intravenously. The composition can be provided as a liquid, a solution, or a solid, and may be provided in combination with any suitable delivery form or vehicle, examples of which include but are not limited to caplets, capsules, tablets, an inhalant or aerosol, etc.

The dose of the composition to be used will necessarily be dependent upon the needs of the individual to whom the composition of the invention is to be administered. These factors include but are not necessarily limited to the weight, age, sex, and medical history of the individual.

\ The following examples are presented to illustrate the present invention. They are not intended to limiting in any manner.

EXAMPLE 1

Ligands for Sequestration of Fe(II) to form paraCEST agents. In FIG. 1 are shown several new pentadentate and tridentate ligands that contain either semicarbazone or acylhydrazone linkages. These ligands might be used to sequester the Fe(II) from cells for imaging. Both types of ligands are neutral over the physiological pH range of 6-8 and are known to permeate cells and sequester Fe(II). The pentadentate ligands bind in a 1:1 ratio to Fe(II) and the tridentate ligands bind in a 2:1 ratio to Fe(II). Depending on pH, the Fe(II) complexes formed may be cationic or neutral.

The ligands sequester Fe(II) from cells, or tissue. Once in the cell, several examples of these ligands have been shown to sequester Fe(II) from possibly a labile Fe(II) pool or from various compartments in the cell. For example, a few of our ligands are targeted to the mitochondria, an iron rich organelle, by using alkyl chains with cationic groups such as phosphonium. Thus, the ligands in FIG. 1 bind Fe(II) sufficiently strongly to sequester Fe(II) from other places with in the cell and are in some cases targeted to special organelles.

Figures 6, 7:
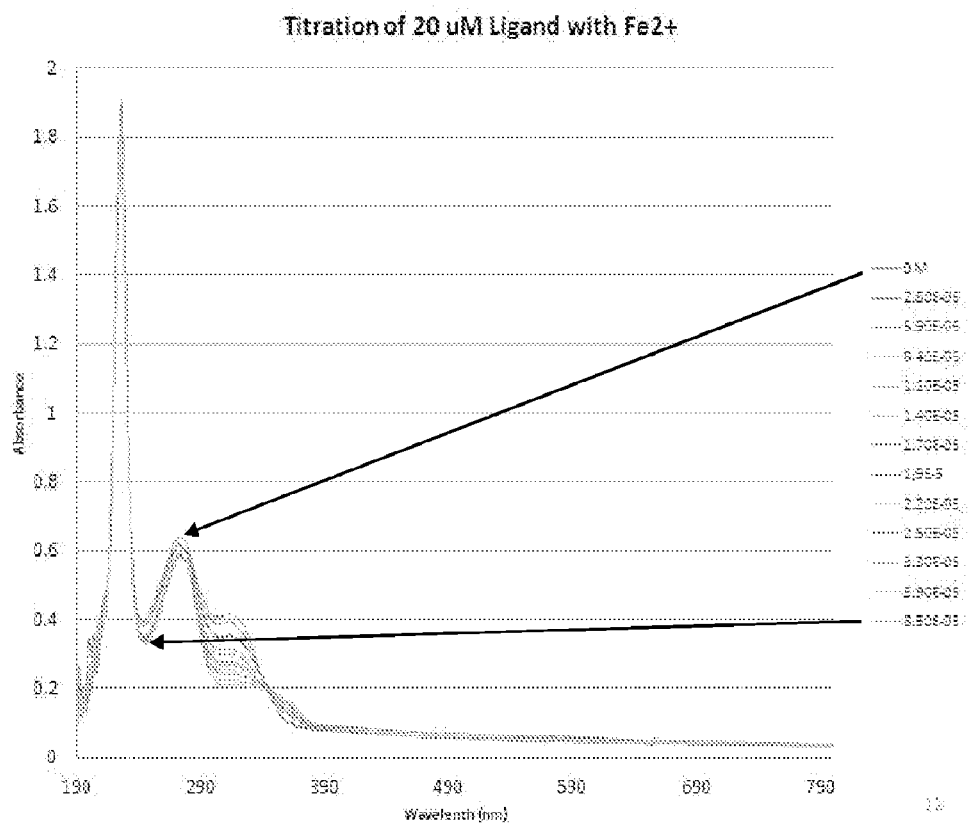
FIG. 6. The UV-visible spectrum of a titration of DAPSC with $Fe(CF_3SO_3)_2$ (top) and a binding isotherm to give a dissociation constant for the Fe(DAPSC) complex of 3.1 micromolar in solutions containing 100 mM NaCl, pH 7.6, 20 mM Hepes buffer.
FIG. 7. Representative binding isotherm obtained from the addition of $Fe(CF_3SO_3)_2$ to DAPSC in a solution containing 100 mM NaCl, 20 mM HEPES buffer, pH 7.6. The Uv-vis peak at 320 was monitored.

The dissociation constant for the Fe(II) complex of the pentadentate semicarbazide ligands are in the micromolar range in water at neutral pH. The dissociation constant for the Fe(II) complexes of the compounds of the disclosure are in the milimolar to micromolar range in water at neutral pH. The binding isotherm for DAPSC with Fe(II) is shown in FIG. 6. Conditions are pH 7.6 and 100 mM NaCl. Tridentate ligands have binding constants that are typically 100-fold weaker. The binding constants depend strongly on pH. At pH values between 6 and 8, the ligands are protonated and are neutral. Most important, there are different Fe(II) complexes that form as a function of pH (FIGS. 8 and 9). The metal ions bind to initially give cationic complexes at weakly acidic pH (6) ([Fe(HL)]$^{2+}$ and [Fe(H$_2$L)]$^{2+}$. At neutral to slightly basic pH, the prominent form is the neutral Fe(II) complex with deprotonated ligand (Fe(L)$_2$ or Fe(L1) FIGS. 8, 9). Note that one or two tridentate ligands may bind to Fe(II). These ligands bind selectively to Fe(II) over Fe(III) under these conditions.

Figure 3:
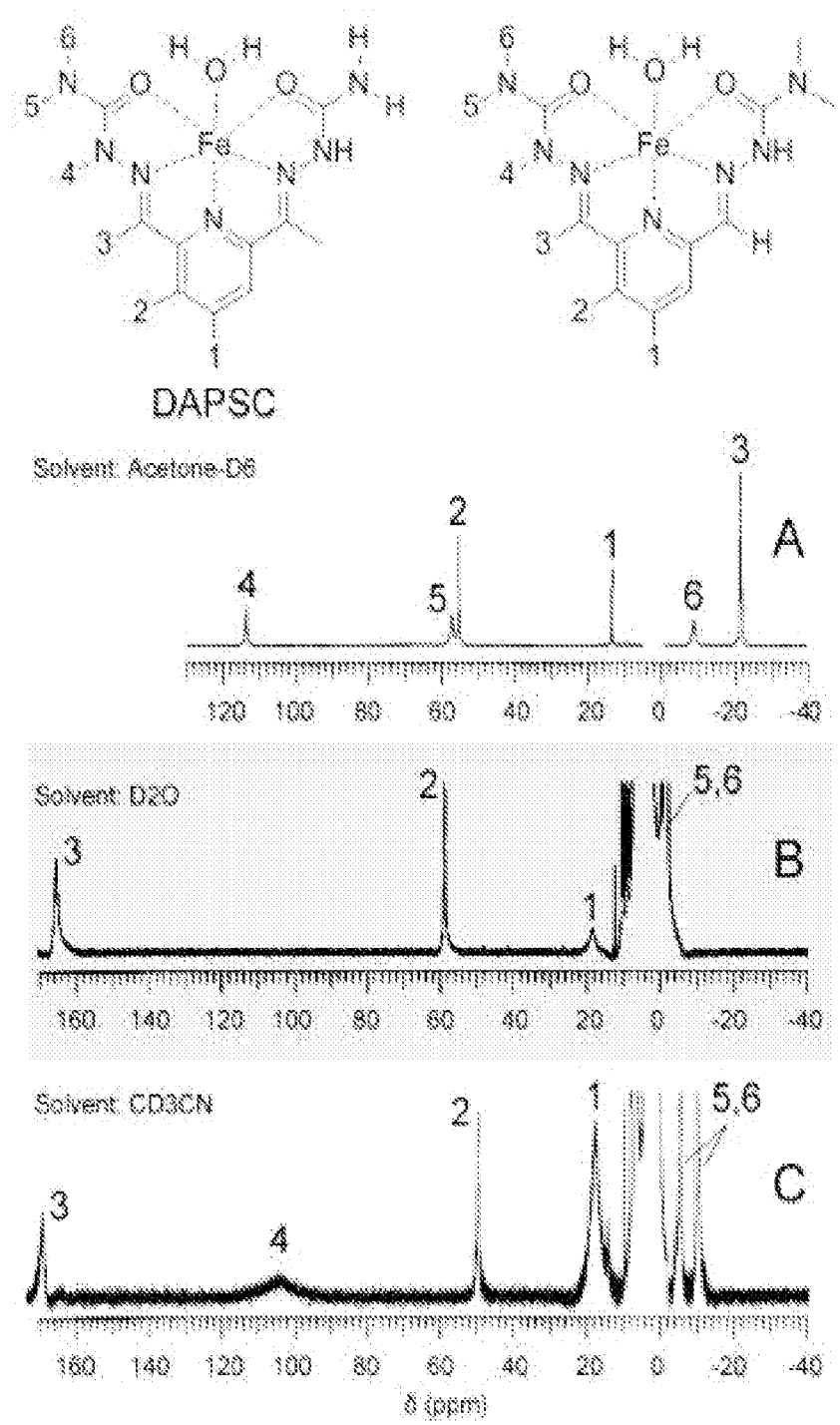
FIG. 3. Examples of $^1$H NMR spectra. The DAPSC (2,6-dialpyridinebis-(hydrazinecarboxamide) iron(II) complex and 2,6-dialpyridinebis-(N,N-dimethylhydrazinecarboxamide) iron complexes are shown with unique proton groups numbered. Spectrum A shows the $^1$H NMR of the Fe(II) (DAPSC) complex in deuterated acetone with their signal assignments. Spectrum B shows the dimethyl derivative in $D_2O$, while spectrum C shows the same complex in deuterated acetonitrile. The important resonance is the exchangeable NH proton resonance at 105 ppm in C.
Figure 4:
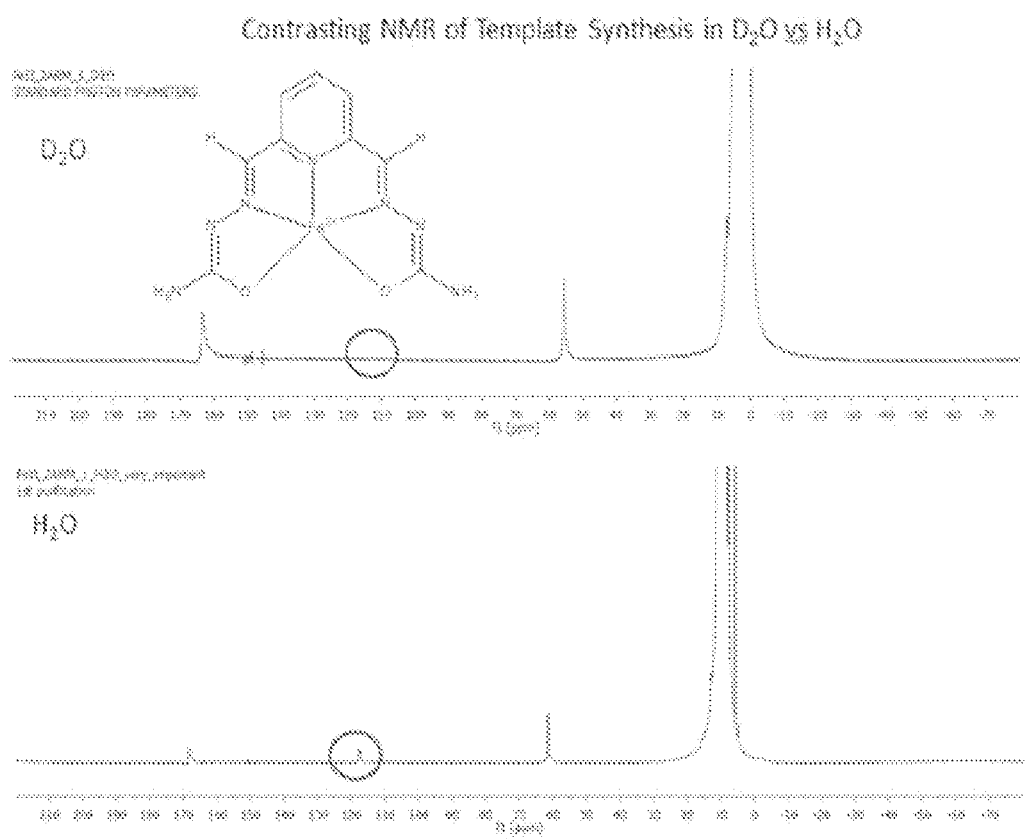
FIG. 4. Representative $^1$H NMR spectrum of Fe(DAPSC) in $D_2O$ and $H_2O$ showing the proton resonance for the exchangeable NH peak.
Figure 10:
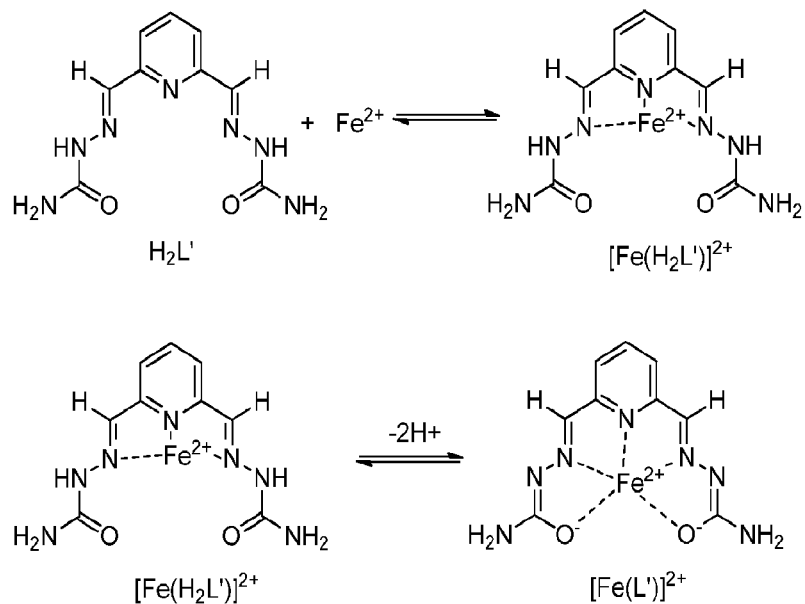
FIG. 10. The Fe(II) complexes formed upon binding of pentadentate semicarbazide ligand.
Figure 11:
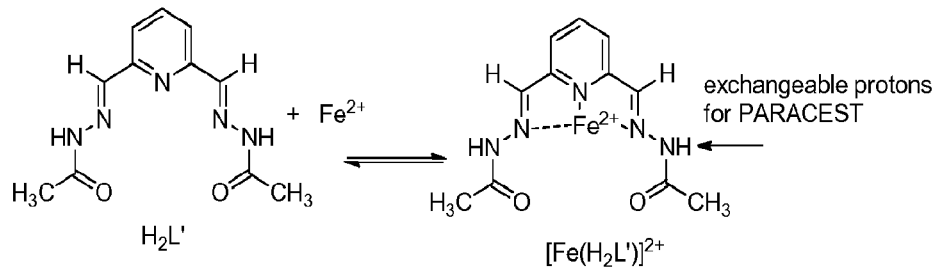
FIG. 11. The Fe(II) complexes formed upon binding to acylhydrazone pentadentate ligand.
Figure 12:
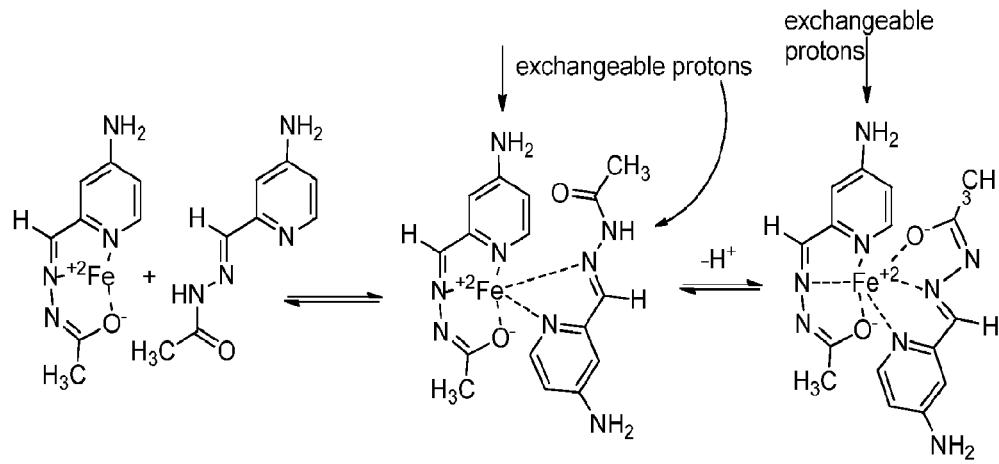
FIG. 12. The Fe(II) complexes formed upon binding to tridentate acylhydrazones.
Figure 13:
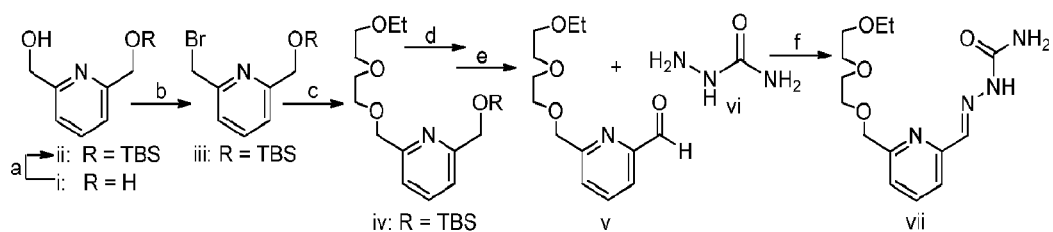
FIG. 13. An example of a synthesis of asymmetric semicarbazone. Reagents and Conditions: (a) TBSC1, imidazole, DMF, r.t.; (b) $CBr_4$, $PPh_3$, diethyl ether, r.t.; (c) 2-(2-ethoxyethoxy)ethanol, NaH, DMF, r.t.; (d) AcOH, $H_2O$, THF, 80° C.; (e) Dess-Martin periodinane, DCM, r.t.; (f) MeOH, AcOH (cat.), 60° C.
Figure 14:
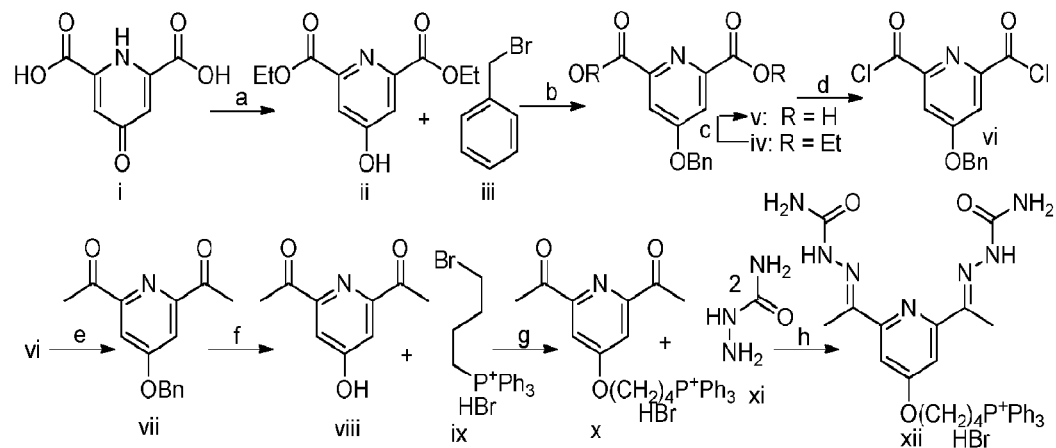
FIG. 14. An example of a reaction scheme for synthesis of symmetric semicarbazones functionalized with cationic group. Reagents and Conditions: (a) EtOH, conc. $H_2SO_4$, 90° C.; (b) $K_2CO_3$, acetonitrile, reflux; (c) 5N NaOH, water-THF, 50° C.; (d) $SOCl_2$, reflux; (e) CuI, MeLi, $Et_2O$, THF, −78° C.; (f) hydrogen, 10% Pd/C, MeOH; (g) TEA, acetonitrile, 60° C.; (h) MeOH, AcOH (cat.), reflux.

The semicarbazide ligands form Fe(II) complexes that have exchangeable NH protons from the semicarbazide terminal NH$_2$ group that are suitable for PARACEST at neutral pH. In addition, at acidic pH values, the protonated complex (Fe(LH) or Fe(H$_2$L')) has a NH group that is suitable for paraCEST (FIG. 5). This exchangeable proton can also be observed in the proton NMR of the complexes (FIGS. 3 and 4). In contrast, the neutral acylhydrazone complexes of Fe(II) (FIGS. 10 and 11) require substituents on the ring that contain NH groups for PARACEST. However, analogous to the semicarbazide complexes, the cationic acylhydrazone complexes have exchangeable NH groups.

Shown in FIG. 5 is a CEST spectrum of the Fe(II) complex of DAPSC, a ligand that is alternately three coordinate or five coordinate, depending on pH. At acidic pH, the complex has three donor groups from the ligand (FIG. 9) to give a CEST peak at 110 ppm for an exchangeable NH. At pH 7.6, the ligand is pentadentate as shown and the terminal NH$_2$ groups are now paramagnetically shifted to give rise to a CEST peak at about 50 ppm.

Complexes that have methyl groups in place of the protons have highly paramagnetically shifted methyl protons (FIG. 3C). These complexes are suitable for using the paramagnetically shifted proton resonances for MRSI. In general, rigid pentadentate ligands such as DAPSC and analogs give relatively narrow proton resonances for MRSI.

To validate the observed CEST spectra of the Fe(II) complexes, CEST imaging will be done at 4.7 T for a phantom array containing solutions of Fe(II) complexes at different concentrations. CEST images will be acquired on a 4.7 Tesla preclinical MR scanner using a 35 mm radiofrequency coil and the ParaVision 3.0.2 research platform (Bruker Biospin, Billerica, Mass.). A pair of gradient-echo MR images will be acquired at 37° C. with a pre-saturation pulse train comprised of five 1 second Gauss pulses (10 μT, 200 μs interpulse delay) either on-resonance (69 ppm) or off-resonance (−69 ppm) of the exchangeable protons. Other key acquisition parameters include: echo time/repetition time=2.1/5010 ms, flip angle=90 deg, acquisition matrix=160×160, slice thickness=2 mm, field of view=32×32 mm, averages=1.

To determine the CEST effect, each image was normalized to the signal intensity of the buffer-only phantom and the normalized image intensity of each phantom was sampled using commercially available software (Analyze 7.0, AnalyzeDirect Inc., Overland Park, Kans.). The percent loss of signal due to PARACEST exchange was calculated using the equation: CEST Effect=1-SI$_{on}$/SI$_{off}$, where SI$_{on}$ is the image intensity of each sample acquired with an on-resonance pre-saturation pulse and SI$_{off}$ is the image intensity acquired with the off-resonance pre-saturation pulse. To create the CEST image (FIG. 6), each data set will be filtered with a spatial low-pass filter (kernel size: 5×5) to improve signal-to-noise, normalized by image intensity of the buffer-only phantom, and then subtracted.

Materials and methods. Instrumentation. All $^1$H NMR spectra were acquired using Varian NMR spectrometers operating at 500, 400, and 300 MHz. Chemical shifts were referenced to residual solvent peaks. Mass spectral data were acquired on a ThermoFinnigan LCQ Advantage IonTrap LC/MS equipped with a Surveyor HPLC system. High-resolution mass spectral data were acquired on a ThermoFinnigan MAT95XL w/ESI II source (NSF Award HE0091977). CEST experiments were acquired on an Inova-400 Spectrometer at room temperature. The pulse power was varied as indicated from B$_1$=450 to 930 Hz with an irradiation time of 2-8 seconds.

Experimental Section. Materials. The iron(II) 2,6-dialpyridinebis(N,N-dimethylhydrazinecarboxamide) complex was prepared by templated synthesis of 2,6-pyridinecarboxaldehyde with N,N-dimethylhydrazinecarboxamide and iron (II) triflate in methanol under anaerobic conditions. The N,N-dimethylhydrazine-carboxamide was prepared in-house in three steps starting from t-butyl hydrazinecarboxylate and dimethylcarbamic chloride. 9.9 g (75 mmol) t-butyl hydrazinecarboxylate was dissolved in 250 mL of chloroform cooled to 0° C. in a round bottom flask fitted with an addition funnel and magnetic stirring. To this was added 11 mL (~1.05 equivalents) triethylamine with magnetic stirring applied. 8.1 g (75 mmol) dimethylcarbamic chloride was dissolved in 50 mL chloroform and placed in the addition funnel. The solution in the funnel was allowed to drip into the flask at a rate of approximately 1 drop per second. The reaction was left and allowed to warm overnight.

Removing the solvent in vacuo yielded white fluffy crystals. Dissolving this material in dichloromethane revealed the presence of at least two distinct species, as a fraction of the material would not go into solution. The DCM solution was placed in a separatory funnel and washed with 100 mL 0.5% HCl, 100 mL saturated aqueous NaHCO$_3$, and then 100 mL H$_2$O. The DCM was then stripped by rotavap to retrieve the material. $^1$H NMR was used to confirm the purity of the product. Yield was 6.3 g (41.5% theoretical) boc-protected N,N-dimethylhydrazinecarboxamide. 2.0 g of the boc-protected material was dissolved in 26 mL of chloroform and deprotected by treatment with 8 mL trifluoacetic acid added dropwise. Stripping the solvent revealed that some TFA remained strongly coordinated to the N,N-dimethylhydrazinecarboxamide. A column with Dowex® 1X2-100 chloride anion exchange resin was used to remove the TFA. The resulting material was waxy, presumably due to coordinated water, but resolved into clear glassy crystals under strong vacuum. Yield was 0.94 g (92.5% theoretical yield).

The Fe(II) complex was prepared in a 250-mL three neck flask was fitted with septum, addition funnel, and condenser. 25 mL of methanol and a magnetic stir bar were added to the flask and the apparatus was degassed with argon. 0.52 g iron(II) triflate (14.8 mmol) was then added and dissolved by magnetic stirring. 0.20 g of 2,6-pyridinecarboxaldehyde (14.8 mmol), 0.34 g of N,N-dimethyl-hydrazinecarboxamide (32.6 mmol), and 0.41 mL of triethylamine were then dissolved in 100 mL methanol and added to the addition funnel. The solution in the addition funnel was allowed to drip at a rate of approximately 1 drop per 3 seconds into the flask. At this point gentle heating was applied and the reaction was maintained at 40° C. for 6 hours. The resulting liquid appeared black, but was seen to be olive green by inspection in the tip of a pipette.

The free ligand was prepared by refluxing 1 equivalent 2,6-pyridinecarboxaldehyde with 2.2 equivalents N,N-dimethyl-hydrazinecarboxamide in methanol with catalytic amounts of glacial acetic acid present. Yield was 88.3% of theoretical after recrystallization from ethyl acetate.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method to obtain an image of at least a portion of a cell, organ, vasculature, or tissue comprising the steps of: contacting the cell, organ, vasculature, or tissue with a compound, wherein the compound does not have Fe(II) complexed to it and becomes complexed to an Fe(II) cation that is an endogenous Fe(II) cation to the cell, organ, vasculature, or tissue, and imaging at least a portion of the cell, organ, vasculature, or tissue to obtain an image of the portion of the cell, organ, vasculature, or tissue, wherein the image is obtained using magnetic resonance imaging, wherein the compound has the following structure:

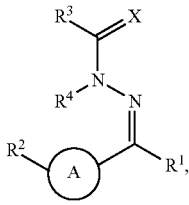

wherein

is a $C_2$ to $C_{12}$ heterocyclic ring system with at least one heteroatom selected from the group consisting of: N atom, O atom, and S atom, $R^1$ is selected from the group consisting of: H and $C_1$ to $C_{12}$ alkyl group, and $R^2$ is selected from the group consisting of: H, $NH_2$, $CH_2C(O)NH_2$, and $CH_2(OCH_2CH_2)_nOCH_2CH_3$, wherein n is from 1 to 6, or $R^2$ is

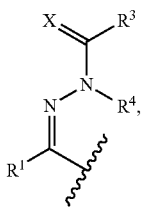

wherein $R^3$ is selected from the group consisting of: $NH_2$, $N(R^5)_2$, and

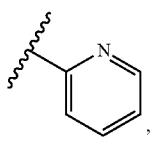

$R^4$ is H or $C_1$ to $C_{12}$ alkyl group; and each $R^5$ is independently selected from H and $C_1$ to $C_{12}$ alkyl group, and X is O or S, wherein the compound has at least one exchangeable proton.

2. The method of claim 1, wherein the cell, organ, vasculature, or tissue is part of an individual.

3. The method of claim 1, wherein the image is obtained using Magnetic Resonance Imaging (MRI).

4. The method of claim 1, wherein the image is obtained using chemical exchange saturation transfer (CEST).

5. The method of claim 1, wherein the image is obtained using paramagnetic chemical exchange saturation transfer (paraCEST).

6. The method of claim 1, wherein the image is obtained using magnetic resonance spectroscopy imaging (MRSI).

7. The method of claim 1, wherein the image is obtained using thermometry.

8. The method of claim 1, wherein the image is obtained using pH mapping.

9. The method of claim 1, wherein

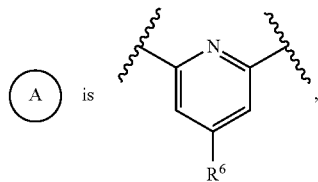

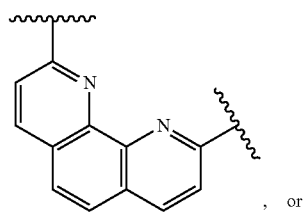

, or

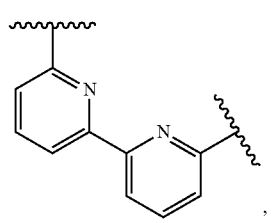

, wherein $R^6$ is selected from the group consisting of: H, $C_1$ to $C_{12}$ alkyl group, ether group, and amino group.

10. The method of claim 1, wherein the compound has the following structure:

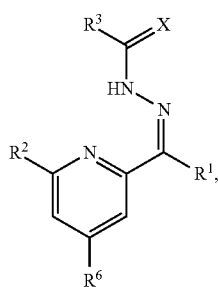

wherein $R^1$ is H or a $C_1$ to $C_{12}$ alkyl group, $R^2$ is H, $R^3$ is $NH_2$, $R^6$ is H, amino group, $C_1$ to $C_{12}$ alkyl group, or ether group, and X is O or S.

11. The method of claim 1, wherein the compound has the following structure:

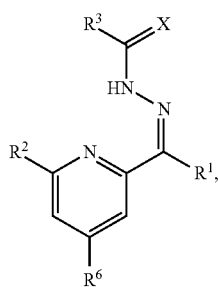

wherein $R^1$ is H or a $C_1$ to $C_{12}$ alkyl group, $R^2$ is $NH_2$ or $CH_2C(O)NH_2$, $R^3$ is

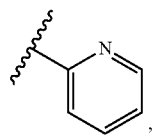, $R^6$ is H, an amino group, $C_1$ to $C_{12}$ alkyl group, or ether group, and X is O or S.

12. The method of claim 1, wherein the compound has the following structure:

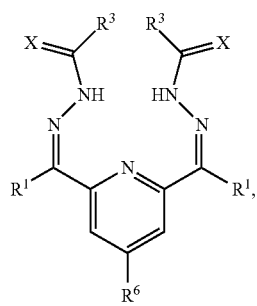

wherein $R^1$ is H or a $C_1$ to $C_{12}$ alkyl group, $R^3$ is $NH_2$ or $N(CH_3)_2$, $R^6$ is H, an amino group, $C_1$ to $C_{12}$ alkyl group, or ether group, and X is O or S.

13. The method of claim 1, wherein the compound has the following structure:

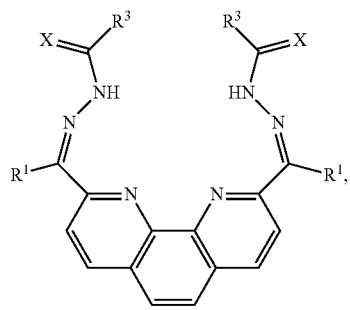

wherein $R^1$ is H or a $C_1$ to $C_{12}$ alkyl group, $R^3$ is $NH_2$ or $N(CH_3)_2$, and X is O or S.

14. The method of claim 1, wherein the compound has the following structure:

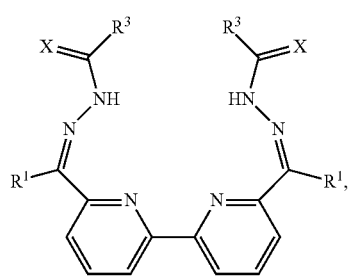

wherein $R^1$ is H or a $C_1$ to $C_{12}$ alkyl group, $R^3$ is $NH_2$ or $N(CH_3)_2$, and X is O or S.

15. The method of claim 1, wherein the compound has the following structure:

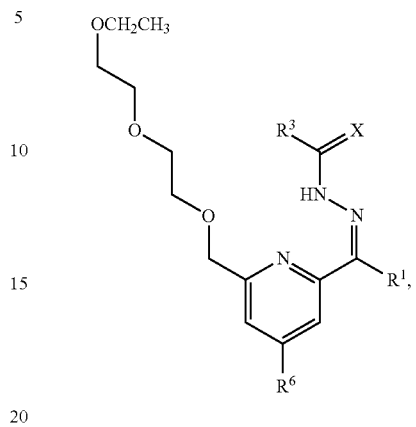

wherein $R^1$ is H or a $C_1$ to $C_{12}$ alkyl group, $R^3$ is $NH_2$ or $N(CH_3)_2$, $R^6$ is H, an amino group, $C_1$ to $C_{12}$ alkyl group, or ether group, and X is O or S.

16. The method of claim 1, wherein the compound has the following structure:

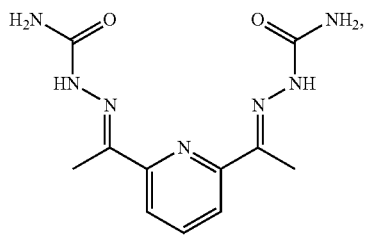

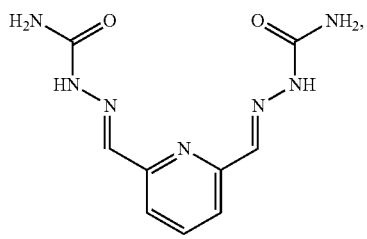

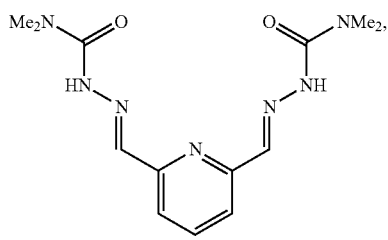

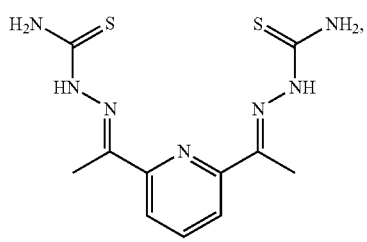

-continued
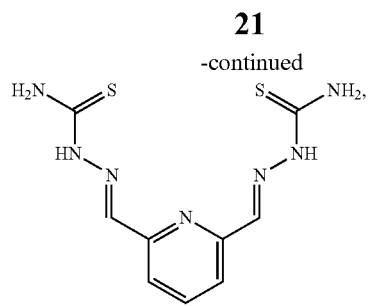
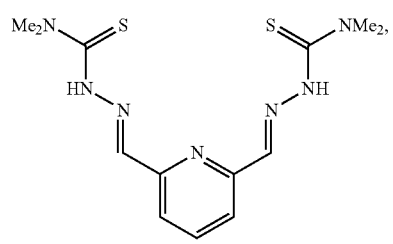
-continued
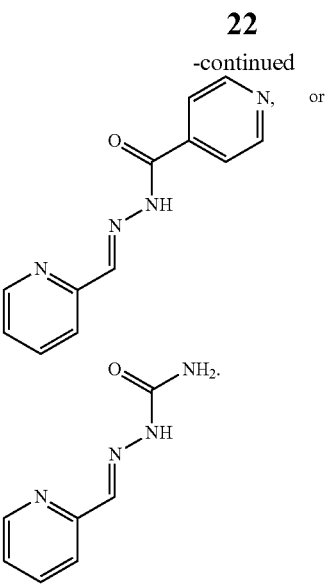
* * * * *